United States Patent [19]
Yamanouchi

[11] Patent Number: 5,863,329
[45] Date of Patent: Jan. 26, 1999

[54] CERAMIC COMPOSITE DOCTOR BLADE

[75] Inventor: Hidenori Yamanouchi, Kagoshima, Japan

[73] Assignee: Kyocera Corporation, Kyoto, Japan

[21] Appl. No.: 937,703

[22] Filed: Sep. 25, 1997

[30] Foreign Application Priority Data

Sep. 30, 1996 [JP] Japan .................................... 8-258153

[51] Int. Cl.$^6$ .............................. B05C 11/02; B05C 1/06; B05C 3/02; B31F 1/12
[52] U.S. Cl. ......................... 118/100; 118/123; 118/126; 118/261; 118/413; 162/281; 399/274
[58] Field of Search .............................. 118/70, 123, 126, 118/104, 261, 100, 413; 101/157, 162, 166, 350.6; 15/255.5; 242/582; 399/274, 284

[56] References Cited

U.S. PATENT DOCUMENTS 4,349,934  9/1982  Margittai ............................. 15/156.51
5,153,033  10/1992  Shibata et al. .......................... 118/123
5,156,682  10/1992  Zimmer .................................... 118/119

*Primary Examiner*—David A. Simmons
*Assistant Examiner*—J. A. Lorengo
*Attorney, Agent, or Firm*—Loeb & Loeb LLP

[57] ABSTRACT

It is an object to obtain a blade 1 with which coating or scraping can satisfactorily be performed and which is able to protect a plate-like member 3 from being broken.

A blade having a ceramic plate-like member 3 having an edge 3a and secured to the surface of an elongated metal plate 2 in the leading end portion of the elongated metal plate 2, wherein the blade 1 is deflected by 10 cm or more in the direction of the thickness thereof owning to the deadweight without breakage of the ceramic plate-like member 3 when the blade 1 is supported at two ends thereof which are apart from each other by 1 m or longer in the lengthwise direction thereof.

3 Claims, 3 Drawing Sheets

CERAMIC COMPOSITE DOCTOR BLADE

BACKGROUND OF THE INVENTION

The present invention relates to a blade for coating the surface of a sheet-like member or that of a cylindrical member with another substance or scraping off a substance from the surface of a member of the foregoing type.

Hitherto, doctor blades have been used in a variety of industrial fields. For example, the doctor blade has been used in a process for coating the surface of paper with resin or a process for coating the same with a heat sensitive material to manufacture heat sensitive paper, a process for coating the surface of sheet-like paper or another member with resin, a process for scraping off excess ink allowed to adhere to the surface of a printing plate and a process for molding rubber or foods into a sheet shape.

A major portion of the doctor blades has been made of a metal material, such as high-speed steel, and arranged in such a way that resin or the like is spread while the resin or the like is being pressed by the edge formed at the leading end of the doctor blade or ink or the like is scraped off. Doctor blades of a type made of a metal material however suffer from a problem in that inevitable wear of the edge of the doctor blade causes uniform coating to be impossible it leads to a fact that the doctor blade must be changed after it has been used for two hours, Thus there arises critical problems in that reliability and working efficiency are unsatisfactory.

To solve the above-mentioned problems, a method has been disclosed in Japanese Patent Publication No. 2-38671, in which a hard film made of tungsten carbide (WC) is thermally sprayed to the end surface of the blade. However, the foregoing blade can be used in only short time of about 80 hours because the hard film is separated during the operation.

Accordingly, a structure has been suggested in which, as disclosed in Japanese Patent Publication No. 2-51398, at least the cutting part of the blade is made of zirconia ceramics.

When the overall body of the doctor blade or the cutting part of the same is made of zirconia ceramics, the thickness must be considerably reduced to 1 mm or smaller. Therefore, if the doctor blade is deflected during the operation, there arises a risk that the doctor blade will be broken. If the blade is formed thick to prevent breakage, the blade cannot easily be deflected. In this case, there arise problems in that coating and scraping cannot easily be performed, thus resulting in that coating is performed nonuniformly and streaky defects take place.

In view of the foregoing, an object of the present invention is to provide a blade which cannot be broken when the blade is deflected during operation or handling and which exhibits excellent wear resistance.

A blade according to the present invention comprises a ceramic plate-like member having an edge and secured to the surface of at elongated metal plate in the leading end portion of the elongated metal plate, wherein the blade is deflected by 10 cm or more in the direction of the thickness thereof owning to the deadweight without breakage of the ceramic plate-like member when the blade is supported at two ends thereof which are apart from each other by 1 m or longer in the lengthwise direction thereof.

In order to satisfactorily perform an operation using the blade, the blade must appropriately be deflected. A variety of studies were performed by the inventor of the present invention. As a result, a preferred result can be obtained by adjusting materials, dimensions and shapes of the metal plate and the ceramic plate-like member and by making the blade to be deflected by 10 cm or more in the direction of the thickness of the blade owning to the deadweight when the blade is supported at two ends thereof which are apart from each other by 1 m or longer in the lengthwise direction thereof. Moreover, a structure in which the ceramic plate-like member is secured to the surface in the leading end portion of the metal plate enables the overall body of the blade to easily be deflected and the ceramic plate-like member to be protected from being broken when the blade is deflected.

A blade according to the present invention comprises a ceramic plate-like member having an edge and secured to the surface of an elongated metal plate in the leading end portion of the elongated metal plate, wherein the apparent Young's modulus $E_A$ (kg/cm²) of the overall body of the blade is defined as follows:

$$1/E_A = V_1/E_1 + V_2/E_2$$

when the Young's modulus of the ceramic plate-like member is $E_1$ (kg/m²), the volume fraction of the same is $V_1$, the Young's modulus of the metal plate is $E_2$ (kg/m²) and the volume fraction of the sane is $V_2$, and the following relationship is satisfied:

$$5 \times 10^{-10} < A < 7 \times 10^{-8}$$

when the cross sectional secondary moment is I (m⁸), weight per unit length is W (kg/m) and $A = 5W/384 E_A I$ That is, value A is a measure indicating the quantity of deflection realized by the deadweight of the blade. When the value A satisfies the above-mentioned range, the blade can be deflected.

A blade according to the present invention comprises a ceramic plate-like member having an edge and secured to the surface of an elongated metal plate in the leading end portion of the elongated metal plate, wherein the following relationship is satisfied:

$$E_1 < 3.0 \times 10^{10}$$

when the fracture toughness level of the ceramic plate-like member is $K_C$ (kg/m$^{3/2}$), the Vickers hardness of the same is H (kg/m²), and the Young's modulus of the same is $E_1$ (kg/m²), and the following relationship is satisfied:

$$2.00 \times 10^{-8} < R < 2.60 \times 10^{-8}$$

when $R = (E_1/H)^{4/5}/(K_C^{1/2} + H^{5/8})$.

That is, the value R is the measure indicating the wear resistance. When the value R satisfies the above-mentioned range, the blade has satisfactory wear resistance and the same can appropriately be worn to be fitted to the shape of the coated surface.

EMBODIMENT

A blade for use in a paper making process will now be described as an embodiment of the present invention.

Figure 1A:
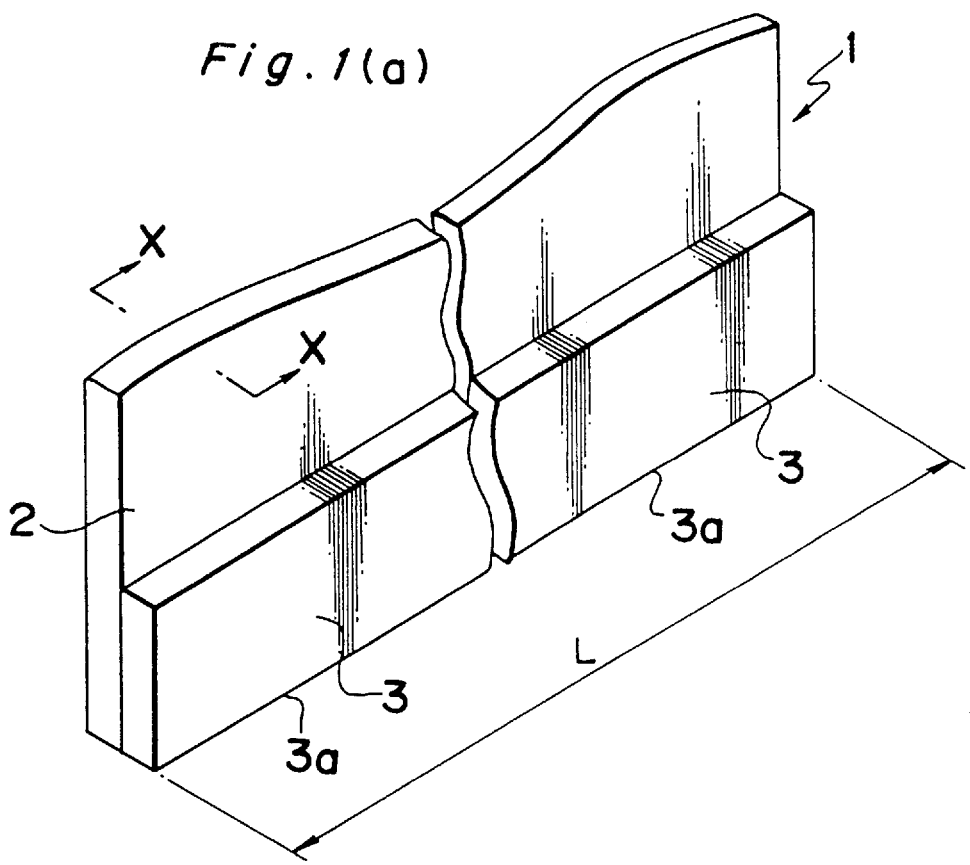
FIG. 1(*a*) is a perspective view showing a blade according to the present invention, and FIG. 1(*b*) is a cross sectional view taken along line X—X shown in FIG. (*a*).
Figure 1B:
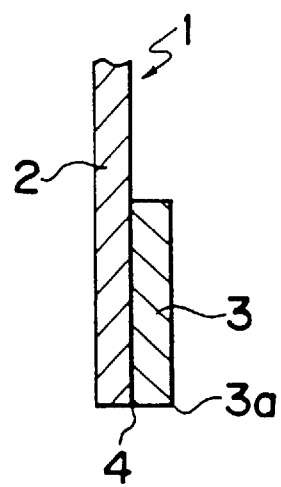
Figure 2:
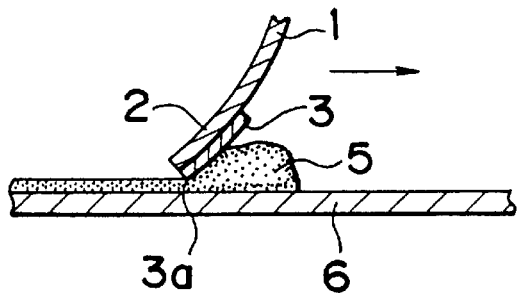
FIG. 2 is a cross sectional view showing a state where the blade according to the present invention is used.

As shown in FIG. 1, a blade 1 according to the present invention has a structure formed by connecting a plate-like member 3 made of ceramics, such as zirconia, to the surface of a metal plate 2 made of high-speed steel in the leading end portion of the metal plate 2 by using an adhesive agent 4. The plate-like member 3 has an edge 3a to enable the blade 1 to scrape off a coat material 5 while the blade 1 is spreading the coat material 5 on the surface of paper 6. Thus, the blade 1 is able to apply the coat material 5 to the surface of the paper 6, as shown in FIG. 2.

Although not shown FIG. 1, a blade 1 according to the present invention has a structure formed by connecting a plate-like member 3 made of ceramics, to the surface of a metal plate 2 by using an adhesive agent 4, the metal plate 2 is able to apply the coat material 5 on the surface of the paper 6. By the above structure. In a use initial stage, a metal plate 2 wear, and a metal plate 2 become the shape along the surface shape of the paper 6, the metal plate 2 is fit to the sape of the surface shape of the paper 6, and a plate-like member 3 is exposed, the wear resistance is improved.

Since the blade 1 has a long overall length L of 1.5 m to 9 m, it is preferable that the plate-like member 3 be integrally formed to have the same length L. As an alternative to this the plate-like member 3 may be sectioned into a plurality of portions each having an edge 3a in such a manner that the edges 3a are aligned after the plate-like member 3 has been connected to the metal plate 2.

Figure 3A:
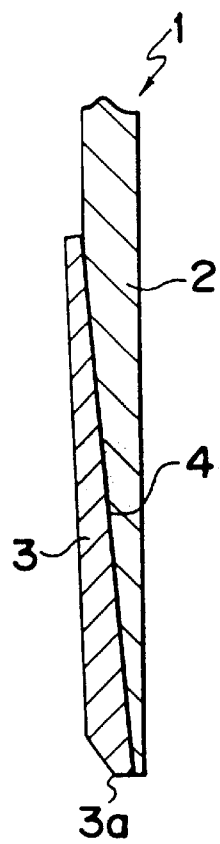
FIGS. 3(*a*) to 3(*c*) are cross sectional views showing another embodiment of the blade according to the present invention.
Figure 3B:
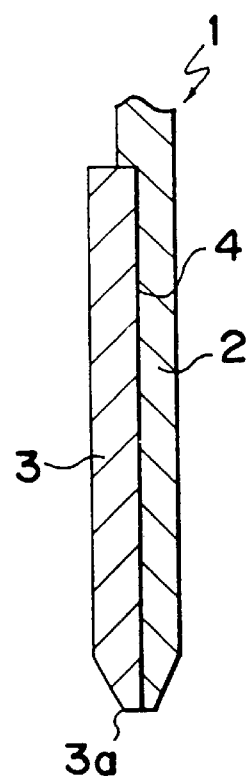
Figure 3C:
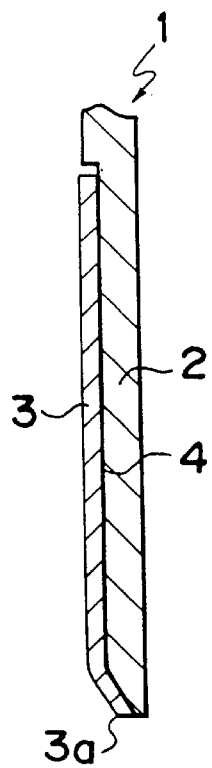

The metal plate 2 and the plate-like member 3 are joined together in such a manner that the adhesive agent 4 is interposed between the flat portions of the metal plate 2 and the plate-like member 3. Note that the joint structure between the metal plate 2 and the plate-like member 3 may be realized in such a manner that the plate-like member 3 is, as shown in FIG. 3, joined to an inclined surface or a recess of the metal plate 2 with the adhesive agent 4. The edge 3a of the plate-like member 3 is not always needed to be a sharp edge. As shown in FIG. 3, the edge 3a may be formed into an in inclined shape or a curved shape.

When the blade 1 is used, the blade 1 must be deflected, as shown in FIG. 2. That is, when the blade 1 is deflected, the edge 3a of the plate-like member 3 can be pressed against the surface of the paper 6. Thus, the coat material 5 can be applied to have a uniform thickness and increased contact strength.

Accordingly, the present invention has an arrangement such that a structure for joining the ceramic plate-like member 3 to the surface of the metal plate 2 in the leading end portion of the metal plate 2 is mainly composed of the metal plate 2. Thus, the blade 1 can easily be deflected.

Figure 4:
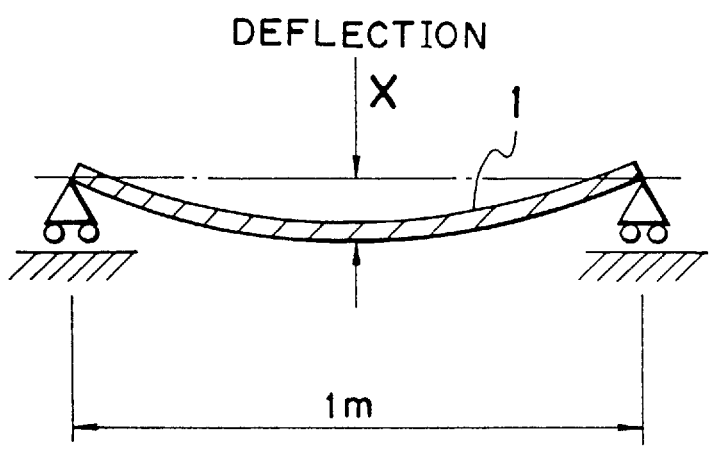
FIG. 4 is a diagram showing a method of measuring the amount of deflection of the blade according to the present invention.

When deflection X realized due to the deadweight was measured to evaluate the deflection of the blade 1 in such a way that the blade 1 was, as shown in FIG. 4, supported at the two ends of the blade 1 which were apart from each other by 1 m in the lengthwise direction of the blade 1, a fact was found that a satisfactory effect was obtained by making the deflection X to be 10 cm or more, preferably 20 cm or more.

If the deflection X is not smaller that 10 cm, preferably not smaller than 20 cm, the blade 1 can sufficiently be deflected when the blade 1 is used as shown in FIG. 2. Therefore, the edge 3a can be pressed against the surface of the paper 6 to cause the coat material 5 to have a uniform thickness and enable the contact strength to be increased.

The deflection X is determined in accordance with the materials, shapes and the dimensions of the metal plate 2 and the plate-like member 3. Therefore, the foregoing factors must be adjusted to make the deflection X to satisfy the above-mentioned range. In actual, the deflection X is substantially determined by the metal plate 2, which is the main portion of the blade 1. In an example case where the metal plate 2 is formed by the high-speed steel, the thickness of the metal plate 2 is required to be 1 mm or smaller.

The deflection X is the value measured when the blade 1 is supported at the two ends which are apart from each other by 1 m. If the length of the blade 1 is not 1 m, the deflection is measured when the blade 1 is supported at the two ends thereof, and then the obtained value is converted by a known method. If the blade 1 is longer than 1 m the deflection X may be obtained by cutting the blade 1 and by supporting the two ends.

An essential portion of the present invention lies in that the ceramic plate-like member 3 must be protected from being broken when the blade 1 is deflected with the deflection X by the deadweight thereof, as shown in FIG. 4. When the blade 1 is used or transported, the above-mentioned deflection X is realized if the worst comes to the worst. Even in the above-mentioned case, the breakage of the plate-like member 3 must be prevented.

Therefore, the material, dimensions and the shape of the plate-like member 3 are needed to be adjusted in such a manner that the plate-like member 3 cannot be broken even if the deflection X is realized. In particular, the material of the plate-like member 3 is an important factor to prevent the breakage. Thus, ceramics having satisfactory strength and toughness must be employed to make the plate-like member 3. Specifically, it is preferable that partially-stabilized zirconia ceramics be employed. The partially-stabilized zirconia ceramics are ceramics mainly composed of $ZrO_2$ and containing one or more types of stabilizers which are $Y_2O_3$, MgO, CaO, $CeO_2$ and $Dy_2O_3$. The partially-stabilized zirconia ceramics is in the form, the main portion of which is a tetragonal crystal phase. The zirconia ceramics of the foregoing type have significantly increased strength and toughness because of stress-induced transformation thereof in which the tetragonal phase is changed into a monoclinic phase when stress is applied to the zirconia ceramics.

The material of the plate-like member 3 is not limited to zirconia ceramics. The required factors are such that the plate-like member 3 has the material, dimensions and the shape in such a manner that the deflection X realized owning to the deadweight is 10 cm or greater and the blade 1 cannot be broken when the blade 1 is supported at the two ends thereof as shown in FIG. 4.

In the present invention, when the Young's modulus of the ceramic plate-like member is $E_1$ (kg/m$^2$), the volume fraction of the same is $V_1$, the Young's modulus of the metal plate is $E_2$ (kg/m$^2$) and the volume fraction of the same is $V_2$, the apparent Young's modulus $E_A$ (kg/cm$^2$) of the overall body of the blade is defined as follows:

$$1/E_A = V_1/E_1 + V_2/E_2$$

Moreover, when the cross sectional secondary moment is I (m$^3$), weight per unit length is W (kg/m) and $A=5W/384E_AI$, the following relationship is satisfied:

$$5\times10^{-10} < A < 7\times10^{-8}$$

The value A is a measure indicating the quantity of deflection realized by the deadweight of the blade 1. When the value A satisfies the above-mentioned range, the blade 1 can be deflected.

In the present invention, when the fracture toughness level of the ceramic plate-like member is $K_C$ (kg/m$^{3/2}$), the Vickers hardness of the same is H (kg/m$^2$), and the Young's modulus of the same is $E_1$ (kg/m$^2$), the following relationship is satisfied:

$$E_1 < 3.0 \times 10^{10}$$

and when $R = (E_1/H)^{4/5}/(K_C^{1/2} \cdot H^{5/8})$, the following relationship is satisfied:

$$2.00 \times 10^{-8} < R < 2.60 \times 10^{-8}$$

The reason why the Young's modulus $E_1$ is made to be smaller than $3.0 \times 10^{10}$ kg/m$^2$ lies in that the plate-like member 3 can easily be deflected as the Young's modulus $E_1$ is made to be smaller to easily follow the deflection of the blade 1. If the plate-like member 3 can easily be deflected, the edge 3a comes in contact with the paper 6 or the like with uniform pressure. As a result, the thickness of the applied film can be uniformed and the finished surface can be smoothed.

The value of R is a measure indicating the wear resistance. The wear resistance is improved in inverse proportion to the value of R. In a case of the doctor blade, the doctor blade must be somewhat worn in an initial stage to be fit to the shape of the surface to be coated in order to prevent uneven coated surface and generation of streaky defect. Therefore, appropriate wear resistance is required. In view of the foregoing, the following relationship must be satisfied:

$$2.00 \times 10^{-8} < R < 2.60 \times 10^{-8}$$

In the foregoing case, satisfactory wear resistance can be realized and thus the lifetime of the blade 1 can be elongated.

The above-mentioned physical property values are measured by using test pieces made of the same material as that of the ceramics forming the blade 1 or test pieces obtained by cutting the blade 1 and each having predetermined dimensions. The Young's modulus $E_1$ is measured by a supersonic pulse method. The fracture toughness $K_C$ is measured by an IF method, and the hardness H is measured by a Vickers hardness method. As an alternative to this, another measuring method may be employed if a known converting equation is available with which the measured value is converted.

Although the description has been performed about the blade for use in the paper making process, the blade according to the present invention may be applied to a variety of purposes, for example, a process for coating the surface of a wood or metal sheet member with resin or the like, a process for scraping off ink allowed to adhere to the surface of a printing plate and a process for molding rubber or foods into a sheet shape.

EXAMPLE 1

An example of the present invention was performed by manufacturing a test blade 1 shown in FIG. 1. The metal plate 2 was formed by high-speed steel to have a thickness of 0.05 cm, a width of 7.5 cm and a length of 100 cm. The plate-like member 3 was made of various ceramics shown in Table 1 and had a thickness of 0.1 cm, a width of 1 cm and a length of 100 cm. The metal plate 2 and the plate-like member 3 were joined up by an epoxy adhesive agent 4.

In Table 1, "zirconia" is in the form of partially-stabilized zirconia ceramics which are mainly made of $ZrO_2$, which contain 3 mol % $Y_2O_3$ and the main portion of which is formed by tetragonal crystal. "alumina" is in the form of alumina ceramics composed of 99% $Al_2O_3$ and a balance composed of $SiO_2$, MgO and the like, "silicon nitride" is in the form of silicon nitride ceramics mainly composed of $Si_3N_4$ and containing $Al_2O_3$ and $Y_2O_3$ as sintering agents and silicon carbide ceramics mainly composed of SiC and containing $Al_2O_3$ and $Y_2O_2$ as sintering agents.

The deflection X realized when each blade 1 was supported at the two ends which were apart from each other by 1 m as shown in FIG. 4 was measured. Moreover, breakage of the plate-like member 3 in the foregoing state was confirmed. Each of the ceramic products having the above-mentioned dimensions was calculated in accordance with the Weibull statistics. In addition, stress generated on the blade in a state where the two ends were supported as described above was obtained by using an equation for calculating stress which was generated under isotropic loads. In accordance with the obtained values, safety ratios were calculated.

Results were as shown in Table 1. According to the results, the deflection X of each blade 1 was a satisfactory amount of 22.7 cm. However, the plate-like members 3 respectively made of alumina, silicon nitride and silicon carbide were broken. On the other hand, the plate-like member 3 made of zirconia was not broken. The foregoing results can as well as be estimated from calculations. In accordance with experiments, the blade 1 can be used practically if the safety ratio is 2 or greater.

Therefore, a fact can be understood from this example that the plate-like member 3 made of zirconia ceramics is able to satisfactorily deflect the blade 1 without breakage of the plate-like member 3.

TABLE 1

| Material of Plate-Like Member | Deflection X (cm) | Breakage | Generated Stress (kg/cm$^2$) |
|---|---|---|---|
| Zirconia | 22.7 | No Breakage | 2121 |
| Alumina | 22.7 | Broken | 3535 |
| Silicon Nitride | 22.7 | Broken | 3838 |
| Silicon Carbide | 22.7 | Broken | 3030 |

| Material of Plate-Like Member | Strength of Product (kg/cm$^2$) | Safety Ratio | Evaluation |
|---|---|---|---|
| Zirconia | 7200 | 3.4 | ◯ |
| Alumina | 2232 | 0.63 | X |
| Silicon Nitride | 3600 | 0.94 | X |
| Silicon Carbide | 4320 | 1.42 | X |

Example 2

As a comparative example, a metal plate 2 having a large thickness of 0.11 cm was manufactured, and then a zirconia ceramics plate-like member 3 was joined so that a blade 1 was manufactured. The blade 1 according to the comparative example was supported at the two ends as shown in FIG. 4. As a result, the plate-like member 3 was not broken. However, the deflection X was 5.7 cm which was smaller than 10 cm.

The blade according to the comparative example and the blade according to the Example 1 having the deflection X of 22.7 cm were subjected to an experiment in which the coat material 5 was applied to the surface of the paper 6 as shown in FIG. 2 so that unevenness of the applied coat material 5 was confirmed.

As a result, the operation using the blade according to the comparative example resulted in clear unevenness being confirmed, while the operation using the blade according to the present invention resulted in the coat material 5 being applied to have uniform thicknesses without no unevenness confirmed. The reason for this is that the blade 1 was deflected to press the edge 3a of the plate-like member 3 against the paper 6. As a result, the coat material 5 was applied to have a uniform thickness.

A fact was understood that the coat material 5 was applied to have uniform thicknesses by making the deflection X to be 10 cm or greater when the blade 1 was supported at the two ends.

Example 3

Similarly to Example 1, blades 1 in each of which the plate-like member 3 was made of zirconia ceramics and the metal plate 2 and the plate-like member 3 were varied were manufactured.

Value A of each sample was calculated in such a manner that when the Young's modulus of the ceramics forming the plate-like member 3 was $E_1$ (kg/m$^2$), the volume fraction of the plate-like member 3 with respect to the overall body of the blade 1 was $V_1$, the Young's modulus of the metal plate 2 was $E_2$ (kg/m$^2$) and the volume fraction of the metal plate 2 with respect to the overall body of the blade 1 was $V_2$, the apparent Young's modulus $E_A$ (kg/cm$^2$) of the overall body of the blade 1 is defined as follows:

$$1/E_A = V_1/E_1 + V_2/E_2$$

Assuming that the cross sectional secondary moment is I (m$^8$) and weight per unit length is W (kg/m$^2$), the value A is expressed as follows:

$$A = 5W/384 E_A I$$

Then, the samples were subjected to experiments similar to those according to Example 2 to confirm unevenness of the applied coat material 5 to evaluate the samples. If the value A satisfied the following relationship as shown in Table 2:

$$5 \times 10^{-10} < A < 7 \times 10^{-8}$$

the coat material 5 was applied to have uniform thickness without unevenness. The reason for this lies in that the blade 1 can appropriately be deflected if the value A satisfies the above-mentioned range to press the edge 3a of the plate-like member 3 against the paper 6, thus enabling the coat material 5 to be applied to have uniform thicknesses.

| Thickness of Metal Plate (mm) | Thickness of plate-Like Member (mm) | Value of A | Streaky Defect and Unevenness | Evaluation |
| --- | --- | --- | --- | --- |
| 0.05 | 0.5 | $2.3 \times 10^{-7}$ | Observed | X |
| 0.10 | 0.5 | $5.7 \times 10^{-8}$ | Not Observed | ○ |
| 0.25 | 0.5 | $9.1 \times 10^{-8}$ | Not Observed | ○ |
| 0.50 | 0.5 | $2.3 \times 10^{-8}$ | Not Observed | ○ |
| 0.75 | 0.5 | $1.0 \times 10^{-8}$ | Not Observed | ○ |
| 1.00 | 0.5 | $5.7 \times 10^{-10}$ | Not Observed | ○ |
| 1.10 | 0.5 | $4.7 \times 10^{-10}$ | Observed | X |
| 1.20 | 0.5 | $3.9 \times 10^{-10}$ | Observed | X |

Example 4

Then, the plate-like members 3 made of the various ceramics were used to examine the wear resistance and uniformity of the applied coat material 5. The metal plate 2 was made of high-speed steel to have a thickness of 0.05 cm, a width of 7.5 cm and a length of 25 cm. The plate-like member 3 was made of each of ceramics shown in Table 3 to have a thickness of 0.05 cm, a width of 0.1 cm and a length of 25 cm. Then, the plate-like member 3 was joined to the metal plate 2.

Among the ceramic materials shown in Table 3, zirconia 1 was the same as zirconia in Example 1, zirconia 2 was obtained by subjecting sintered zirconia 1 to a hot isostatic pressing (HIP) process, zirconia 3 was obtained by adding about 20% $Al_2O_3$ to zirconia 1, after which the HIP process was performed, zirconia 4 was obtained by adding $CeO_2$ and $Dy_2O_3$ as stabilizer to the main component which was $ZrO_2$. Silicon carbide 2 was mainly composed of β-SiC and arranged to contain B and C to serve as sintering agents. Thermet was a combined-type sintered material consisting of a hard component, the main component of which was TiC, TiN and the like and iron family metal.

The respective blades were subjected to experiments in which the coat material 5 was applied to the surface of the paper 6, as shown in FIG. 2. After the experiment was performed for 150 hours, the state or wear of the edge 3a of the blade and the state of the applied coat material 5 were observed.

The state of wear was evaluated in accordance with rearward movement of the edge 3a from the leading end because of the wear, while the state of the applied coat material 5 was evaluated such that existence of streaky defects on the surface of the paper was visually checked.

Results were as shown in Tables 3 and 4. As shown in Tables 3 and 4, the samples having the value of R satisfying $2.00 \times 10^{-8} < R < 2.60 \times 10^{-8}$ and the Young's modulus $E_1$ of smaller than $3.0 \times 10^{10}$ kg/m$^2$ resulted in free from unevenness of the coat material 5. Therefore, a fact can be understood that samples satisfying the two factors enables the coat material to be uniformly applied and the lifetime to be elongated.

TABLE 3

| Material of Plate-Like Member | Toughness kc (kg/m$^{3/2}$) | Hardness H (kg/m$^3$) | Young's modulus $E_1$ (kg/m$^2$) | Value of R |
| --- | --- | --- | --- | --- |
| Zirconia 1 | $6.8 \times 10^5$ | $1.25 \times 10^8$ | $2.1 \times 10^{10}$ | $2.39 \times 10^{-8}$ |
| Zirconia 2 | $6.0 \times 10^5$ | $1.3 \times 10^8$ | $2.2 \times 10^{10}$ | $2.5 \times 10^{-8}$ |
| Zirconia 3 | $7.0 \times 10^5$ | $1.35 \times 10^8$ | $2.6 \times 10^{10}$ | $2.5 \times 10^{-8}$ |
| Zirconia 4 | $1.2 \times 10^5$ | $1.1 \times 10^8$ | $2.1 \times 10^{10}$ | $2.16 \times 10^{-8}$ |
| Alumina | $4.3 \times 10^5$ | $1.79 \times 10^8$ | $3.7 \times 10^{10}$ | $2.83 \times 10^{-8}$ |
| Silicon Nitride | $5.8 \times 10^5$ | $1.4 \times 10^8$ | $3.0 \times 10^{10}$ | $2.83 \times 10^{-8}$ |
| Silicon Carbide 1 | $5.7 \times 10^5$ | $2.35 \times 10^8$ | $4.39 \times 10^{10}$ | $1.92 \times 10^{-8}$ |
| Silicon Carbide 2 | $3.5 \times 10^5$ | $2.35 \times 10^8$ | $3.79 \times 10^{10}$ | $2.17 \times 10^{-8}$ |
| Thermet | $8.7 \times 10^5$ | $1.65 \times 10^8$ | $4.5 \times 10^{10}$ | $2.62 \times 10^{-8}$ |

TABLE 4

| Material of Plate-Like Member | Evaluated Wear Resistance | Unevenness of Surface of Paper | Total Evaluation |
| --- | --- | --- | --- |
| Zirconia 1 | ○ | Not Observed | ○ |
| Zirconia 2 | ○ | Not Observed | ○ |
| Zirconia 3 | ○ | Not Observed | ○ |
| Zirconia 4 | ○ | Not Observed | ○ |
| Alumina | ○ | Observed | X |
| Silicon Nitride | ○ | Observed | X |
| Silicon Carbide 1 | ⊙ | Observed | X |

TABLE 4-continued

| Material of Plate-Like Member | Evaluated Wear Resistance | Unevenness of Surface of Paper | Total Evaluation |
|---|---|---|---|
| Silicon Carbide 2 | ⊚ | Observed | X |
| Thermet | ◯ | Observed | X |

As described above, according to the present invention, there is provided a blade comprising a ceramic plate-like member having an edge and secured to the surface of au elongated metal plate in the leading end portion of the elongated metal plate, wherein the blade is deflected by 10 cm or more in the direction of the thickness thereof owning to the deadweight without breakage of the ceramic plate-like member when the blade is supported at two ends thereof which are apart from each other by 1 m or longer in the lengthwise direction thereof. Thus, the blade can appropriately be deflected when the blade is used. Therefore, coating or scraping can satisfactorily be performed. Moreover, the plate-like member is not broken during use or transportation.

According to the present invention, thee is provided a blade comprising a ceramic plate-like member having an edge and secured to the surface of an elongated metal plate in the leading end portion of the elongated metal plate, wherein the apparent Young's modulus $E_A$ (kg/cm$^2$) of the overall body of the blade is defined as follows:

$$1/E_A = V_1/E_1 + V_2/E_2$$

when the Young's modulus of the ceramic plate-like member is $E_1$ (kg/m$^2$), the volume fraction of the same is $V_1$, the Young's modulus of the metal plate is $E_2$ (kg/m$^2$) and the volume fraction of the same is $V_2$, and the following relationship is satisfied:

$$5 \times 10^{-10} < A < 7 \times 10^{-8}$$

when the cross sectional secondary moment is I (m$^8$), weight per unit length is W (kg/m) and $A = 5W/384E_A I$. Since the blade can appropriately be deflected during use, coating or scraping can satisfactorily be performed.

According to the present invention, there is provided a blade comprising a ceramic plate-like member having an edge and secured to the surface of an elongated metal plate in the leading end portion of the elongated metal plate, wherein the following relationship is satisfied:

$$E_1 < 3.0 \times 10^{10}$$

when the fracture toughness level of the ceramic plate-like member is $K_C$ (kg/m$^{3/2}$), the Vickers hardness of the same is H (kg/m$^2$), and the Young's modulus of the same is $E_1$ (kg/m$^2$), and the following relationship is satisfied:

$$2.00 \times 10^{-8} < R < 2.60 \times 10^{-8}$$

when $R = (E_1/H)^{4/5}/(K_C^{1/2} \cdot H^{5/8})$. Thus, the edge of the blade can satisfactorily be brought into close contact with a required member. Moreover, the wear resistance of the blade can be improved.

What is claimed is:

1. A blade comprising a ceramic plate-like member having an edge and secured to the surface of an elongated metal plate in the leading end portion of the elongated metal plate, wherein the blade is deflected by 10 cm or more in the direction of the thickness thereof owning to the deadweight without breakage of the ceramic plate-like member when the blade is supported at two ends thereof which are apart from each other by 1 m or longer in the lengthwise direction thereof.

2. A blade comprising a ceramic plate-like member having an edge and secured to the surface of an elongated metal plate in the leading end portion of the elongated metal plate, wherein the apparent Young's modulus $E_A$ (kg/cm$^2$) of the overall body of the blade is defined as follows:

$$1/E_A = V_1/E_1 + V_2/E_2$$

when the Young's modulus of the ceramic plate-like member is $E_1$ (kg/m$^2$), the volume fraction of the same is $V_1$, the Young's modulus of the metal plate is $E_2$ (kg/m$^2$) and the volume fraction of the same is $V_2$, and the following relationship is satisfied:

$$5 \times 10^{-10} < A < 7 \times 10^{-8}$$

when the cross sectional secondary moment is I (m$^3$), weight per unit length is W (kg/m) and $A = 5W/384E_A I$.

3. A blade comprising a ceramic plate-like member having an edge and secured to the surface of an elongated metal plate in the leading end portion of the elongated metal plate, wherein the following relationship is satisfied:

$$E_2 < 3.0 \times 10^{10}$$

when the fracture toughness level of the ceramic plate-like member is $K_C$ (Kg/m$^{3/2}$), the Vickers hardness of the same is H (kg/m$^2$), and the Young's modulus of the same is $E_1$ (kg/m$^2$), and the following relationship is satisfied:

$$2.00 \times 10^{-8} < R < 2.60 \times 10^{-8}$$

when $R = (E_1/H)^{4/5}/(K_C^{1/2} \cdot H^{5/8})$.

* * * * *